(12) United States Patent
Lentner et al.

(10) Patent No.: US 11,333,192 B1
(45) Date of Patent: May 17, 2022

(54) POLYAXIAL BALL AND SOCKET FASTENER WITH RING CONTAINMENT

(71) Applicant: Ortho Innovations, LLC, Palm Beach Gardens, FL (US)

(72) Inventors: Greg Lentner, Maumee, OH (US); John E. Hammill, Sr., Maumee, OH (US)

(73) Assignee: Ortho Innovations, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/457,347

(22) Filed: Dec. 2, 2021

(51) Int. Cl.
*F16C 11/06* (2006.01)
*A61B 17/70* (2006.01)

(52) U.S. Cl.
CPC ...... *F16C 11/0623* (2013.01); *A61B 17/7032* (2013.01); *A61B 17/7037* (2013.01)

(58) Field of Classification Search
CPC .............. F16C 11/0623; F16C 11/0619; Y10T 403/7041; Y10T 403/32311; Y10T 403/32336; A61B 17/7032; A61B 17/7037; A61B 17/7038; A61B 17/7035; A61B 17/7034
See application file for complete search history.

(56) References Cited

U.S. PATENT DOCUMENTS

| | | |
|---|---|---|
| 3,433,510 A | 3/1969 | Hulterstrum |
| 4,273,116 A | 6/1981 | Chiquet |
| 4,483,334 A | 11/1984 | Murray |
| 4,693,240 A | 9/1987 | Evans |
| 4,708,510 A | 11/1987 | McConnell et al. |
| 4,836,196 A | 6/1989 | Park et al. |
| 4,854,304 A | 8/1989 | Zielke |
| 4,887,595 A | 12/1989 | Heinig et al. |
| 4,887,596 A | 12/1989 | Sherman |
| 4,946,458 A | 8/1990 | Harms et al. |
| 5,002,542 A | 3/1991 | Frigg |
| 5,129,900 A | 7/1992 | Asher et al. |
| 5,133,717 A | 7/1992 | Chopin |
| 5,501,684 A | 3/1996 | Schlapfer et al. |
| 5,549,608 A | 8/1996 | Errico et al. |
| 5,569,247 A | 10/1996 | Morrison |
| 5,591,166 A | 1/1997 | Bernhardt et al. |
| 5,716,357 A | 2/1998 | Rogozinski |
| 5,800,435 A | 9/1998 | Errico et al. |
| 6,485,491 B1 | 11/2002 | Farris et al. |
| 6,565,567 B1 | 5/2003 | Haider |
| 6,672,788 B2 | 1/2004 | Hathaway |

(Continued)

*Primary Examiner* — Daniel J Wiley
(74) *Attorney, Agent, or Firm* — McHale & Slavin, P.A.

(57) ABSTRACT

A bottom loading fastening system that consists of the polyaxial ball and socket joint used in conjunction with an anchoring bone screw. The system allows attachment of a connector assembly to the anchoring bone screw having a spherical ball connector using a locking ring positioned in a locking ring slot. Upon installation, the locking ring is moved to a ring containment slot to expand a retainer ring, allowing passage of a bone screw spherical ball, the retainer ring forcing the locking ring back to the locking ring slot, thereby permanently attaching the connector assembly to the anchoring bone screw. Movement of the locking ring from the ring containment slot provides an audible sound and tactile indication that the locking ring has secured the connector assembly to the bone screw.

8 Claims, 9 Drawing Sheets

(56) References Cited

U.S. PATENT DOCUMENTS

| | | | |
|---|---|---|---|
| 6,716,214 | B1 | 4/2004 | Jackson |
| 7,066,937 | B2 | 6/2006 | Shluzas |
| 7,445,627 | B2 | 11/2008 | Hawkes et al. |
| 7,942,909 | B2 | 5/2011 | Hammill, Sr. et al. |
| 7,942,911 | B2 | 5/2011 | Doubler et al. |
| 7,947,065 | B2 | 5/2011 | Hammill, Sr. et al. |
| 7,951,173 | B2 | 5/2011 | Hammill, Sr. et al. |
| 8,075,603 | B2 | 12/2011 | Hammill, Sr. et al. |
| 8,197,518 | B2 | 6/2012 | Hammill, Sr. et al. |
| 8,465,530 | B2 | 6/2013 | Hammill, Sr. et al. |
| 8,556,938 | B2 * | 10/2013 | Jackson ............. A61B 17/7008 606/269 |
| 8,663,291 | B2 * | 3/2014 | Doubler ............. A61B 17/7037 606/270 |
| 9,060,814 | B2 | 6/2015 | Doubler et al. |
| 10,258,385 | B1 | 4/2019 | Doubler et al. |
| 10,285,738 | B1 | 5/2019 | Doubler et al. |
| 10,687,857 | B2 * | 6/2020 | Hammer ............ A61B 17/7037 |
| 11,020,150 | B1 | 6/2021 | Doubler et al. |
| 11,141,199 | B1 | 10/2021 | Doubler et al. |
| 2017/0333085 | A1 * | 11/2017 | Jackson ............... A61B 17/863 |

\* cited by examiner

POLYAXIAL BALL AND SOCKET FASTENER WITH RING CONTAINMENT

FIELD OF THE INVENTION

This invention is directed to the field of ball and socket fasteners; and in particular, to a polyaxial ball and socket fastener having a locking ring slot.

BACKGROUND OF THE INVENTION

In the field of spinal pathologies, the development of spinal fixation devices represents a major medical breakthrough. Surgically implanted fixation systems are commonly used to correct a variety of back structure problems, including those which occur as a result of trauma or improper development during growth. A commonly applied fixation system includes the use of one or more stabilizing rods aligned in a desired orientation with respect to a patient's spine. Anchoring screws with connectors are inserted into the patient's spinal bones and used to link the rods to stabilize the spine. A variety of designs exist, with each design addressing various aspects of the difficulties that arise when one re-shapes an individual's spine to follow a preferred curvature. Common to all spinal implant systems is the necessity for proper anchoring to the bone to provide support for the aforementioned components. The use of a polyaxial design has proven very effective in allowing a surgeon the flexibility to secure an installation with minimal strain on the individual.

In a common embodiment, the screw based device is located in bone structure, and typically includes a polyaxial saddle forming a connector member for securing to a connecting rod. Unfortunately, the condition of the bone structure needed to support the threaded shank of a screw cannot be determined until surgery has begun. Bone is not uniform in strength or position, requiring the surgeon to have access to a large inventory of various sized implants to be immediately available during every surgery. The surgeon must search through the inventory to locate the device required.

Once the implant combination is chosen, the anchoring screw may require angular insertion due to muscle structure or nerve locations. Any movement of muscle and other tissue increases the difficulty of the operation and can be a major trauma to the patient. Bone condition may also require oversized threads to achieve a suitable purchase to the bone. Consequently, the surgeon must maintain a large inventory of anchoring devices, or have a vendor standing by with a large inventory of anchoring devices that will hopefully meet the individual requirements. Bottom loading pedicle screw systems reduce inventory, allowing the use of various sized anchoring members for attachment to a connector assembly. The attachment to the saddle connector assembly is a critical requirement which can employ a locking ring that allows the spherical ball connector of an anchor to attach thereto. There are a number of configurations that employ a locking ring. What is lacking in the art is a device that employs a ring containment area for use in combination with a retainer ring.

Disclosures related to polyaxial pedicle screws are exemplified by the following U.S. Pat. Nos. 7,066,937; 7,947,065; 8,075,603; 6,485,491; 5,133,717; 5,129,900; 4,887,595; 4,946,458; 5,002,542; 4,854,304; 4,887,596; 4,836,196; 5,800,435; 5,591,166; 5,569,247; 5,716,357; 5,129,900; 5,549,608; 6,716,214; 6,565,567; 5,501,684; 4,693,240; 4,483,334; 4,273,116; 6,672,788; 4,708,510; 3,433,510; 7,445,627; 7,942,911; 7,942,909; 7,951,173; 8,197,518; 8,465,530; 9,060,814; 10,258,385; 10,285,738; 11,141,199 and 11,020,150.

SUMMARY OF THE INVENTION

Briefly, the present invention is a modular, bottom loading polyaxial ball and socket joint fixation system capable of snap together assembly. The fixation system includes a threaded shank with a spherical ball connector on the opposite end of the threaded shank. The threaded shank is for anchoring to bone, and the spherical ball attaches to a connector assembly. The connector assembly includes a U-shaped upper connector member with a movable saddle. A lower connector member is welded to the upper connector member, forming a ring containment slot for receipt of a retainer ring. A locking ring is secured in a locking ring slot by a spring loaded saddle. The spherical ball of a bone screw is inserted into the connector assembly, the spherical ball moves a locking ring from a locking ring slot into a ring containment slot, causing the retainer ring to expand. The ring containment slot allows only the horizontal displacement of the retainer ring. The spring loaded saddle prevents the locking ring from moving past the ring containment slot. Upon the widest portion of the spherical ball passing the ring containment slot, the locking ring returns to the locking ring slot and the retainer ring remains in the ring containment slot. With the retainer ring returned to the locking ring slot, the spherical ball is permanently captured by the connector assembly.

A set screw is utilized to press a connecting rod into contact with the saddle located over the spherical ball, simultaneously causing the lower portion of the spherical ball connector to wedge against the inner surface of the locking ring, immobilizing the connection. In the preferred embodiment, the saddle employs compression springs to keep the connector assembly in position during installation. This allows a surgeon to easily move the connector assembly into a selected position; and the angular position of the connector assembly will remain the same to facilitate installing of connecting rods. The system is modular employing a collection of anchoring assemblies that are linked, via various connectors, to strategically arranged stabilizing rods. The connector assemblies are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Accordingly, it is an objective of the present invention to teach the use of a bottom loading polyaxial ball and socket fastener for use in a spinal stabilization system utilizing a retainer ring expandable within a ring containment slot by a locking ring held in a locking ring slot for purposes of installing the spherical ball of a fastener, the locking ring returning to the locking ring slot to prevent removal of the installed spherical ball.

Another objective of the invention is to disclose the use of a polyaxial ball and socket system that is capable of securing various anchors to various connector members so as to reduce the amount of inventory required to meet a particular installation.

It is an additional objective of the present invention to provide a connector assembly that includes a locking ring locking mechanism that is simple, strong and reliable; wherein a connector assembly is preloaded with a locking ring and retainer ring. Once the locking ring is moved from a locking ring slot to a ring containment slot, the retainer ring is temporarily expanded to allow the spherical ball to pass before the locking ring is returned to the locking ring slot. The locking ring is held in place by an interference fit beneath the spherical ball and the locking ring slot walls.

Another objective of the invention is to provide a spinal fixation system that has an audible sound and tactile feel when the spherical ball causes the locking ring to release from the retainer ring.

Other objectives and advantages of this invention will become apparent from the following description taken in conjunction with the accompanying drawings, wherein are set forth, by way of illustration and example, certain embodiments of this invention. The drawings constitute a part of this specification, include exemplary embodiments of the present invention, and illustrate various objects and features thereof.

DETAILED DESCRIPTION OF THE PREFERRED EMBODIMENT

Figure 1:
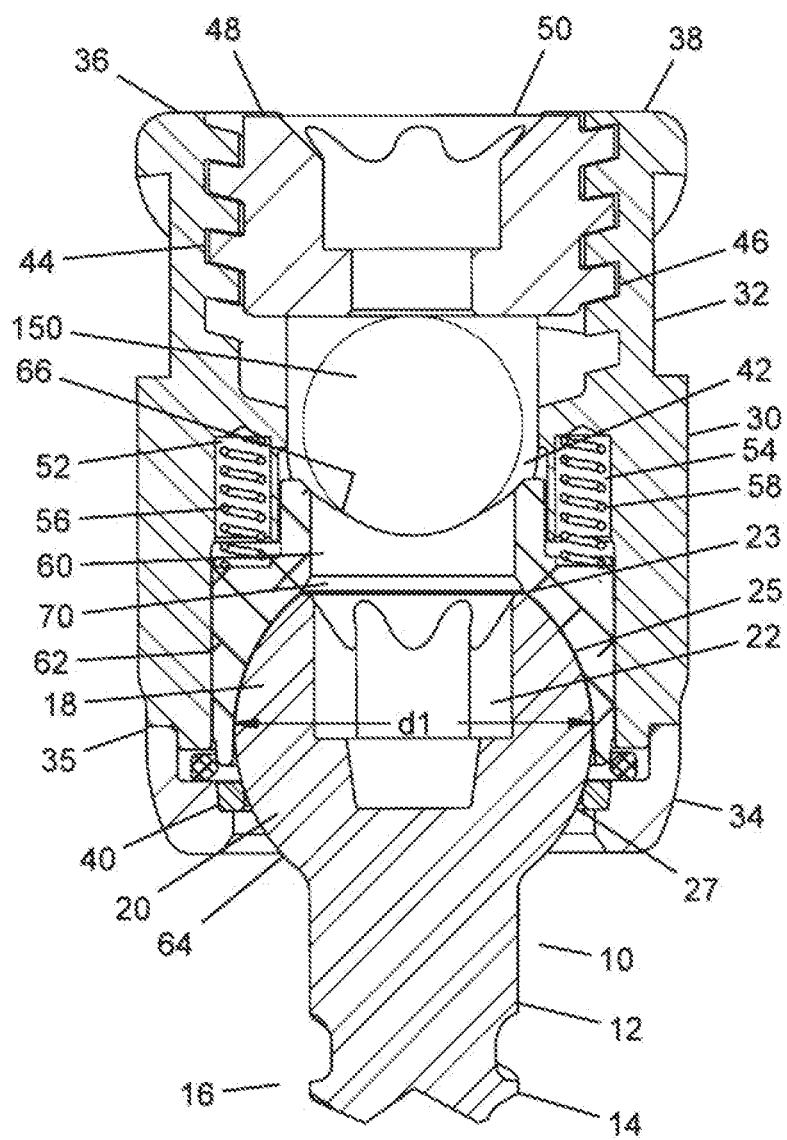
FIG. 1 is a cross-sectional side view of a bone screw anchor member and a rod secured to a connector assembly.

While the present invention is susceptible of embodiments in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to the Figures, disclosed is an exemplary embodiment of the polyaxial ball and socket fastening system adapted for use in a spinal fixation system. The fastening system includes an anchor member (10) formed from a shank (12) having bone threads (14) formed along a first end (16). It is important to note that the proportions of the anchor member (10) depicted are for illustrative purposes only and variations in the length of the shank, diameter of the screw, thread pitch, thread length, number of thread leads, shank induced compression and the like may be varied without departing from the scope of the invention.

At the distal upper end (18) of the shank (12) is a ball-shaped spherical ball connector (20) having a diameter dl. A driver receptacle (22), which may be configured as a plurality of recesses or a single recess for an insertable driver tool, is located along the top (23) of the spherical ball connector (20) for use in installing the anchor member (10) by use of a driving tool, not shown. It should be noted that the driver receptacle (22) may be any shape, male or female, suitable for cooperation with a driving tool to rotate the anchor member (10) into its final position. The spherical ball connector (20) has an upper surface (25) generally defined from the diameter dl to the top end (23), and a lower surface (27) generally defined from the diameter dl to the proximal end forming a shank (12).

A connector assembly (30) is securable to the anchor member (10); the connector assembly (30) including an upper connector member (32) to be attached to a lower connector member (34) by weldment (35). Upon attachment by the weldment (35), the upper connector member (32) and the lower connector member (34) form a locking ring slot (40) therebetween. The upper connector member (32) is further defined by a first side wall (36) and a second side wall (38) forming an opening (42). The first side wall (36) has threads (44) along an upper portion thereof, with cooperating threads (46) placed along an upper portion of the second side wall (38). A centrally disposed opening (48) permits insertion of a driving tool, not shown, for use in mounting the anchor member (10) by engaging of the driver receptacle (22). A set screw (50) is operatively associated with the threaded side walls (36) and (38). The upper connector member (32) includes first and second compression spring sockets (52, 54) positioned on each side of the aperture (48) for receipt of compression springs (56) and (58). It should be noted that while the compression springs (56) and (58) are illustrated as coil springs, any spring or resilient type member suitable for displacing the saddle component may be utilized without departing from the scope of the invention. Such springs or resilient members may include, but should not be limited to, Belleville type springs, leaf springs, polymeric members, and suitable combinations thereof.

A saddle member (60) having a cylindrical sidewall (62) with a centrally located opening (64) is slidably insertable into the upper connector member (32). An upper surface (66) of the saddle member (60) is concave shaped for receipt of a connection rod (150). A lower surface (70) of the saddle member (60) is spherical shaped and coincides with the shape of the spherical ball (20). The upper surface (66) of the saddle member (60) provides additional surface area for contact with a connecting rod (150) and may include a knurled or otherwise modified surface finish adapted to enhance gripping power between the rod (150) and the connector member (32); the saddle member (60) forming a lower cavity (74) constructed and arranged to cooperate and frictionally engage the spherical ball (20) to prevent movement of the anchor member (10) in relation to the connector assembly (30) when fully assembled.

The locking ring slot (40) is formed by a bottom surface (82) and a side surface (84) for receipt of a locking ring (100); the locking ring (100) having a flat upper surface (102), flat outer surface (104), flat lower surface (106) and an inner surface (108) having a beveled upper edge (110) and a beveled lower edge (112), the locking ring (100) has a split making it a non-continuous ring. A ring containment slot (118) is formed by a lower surface (120) with an outer wall (122) and the lower edge of the connector (123). A retainer ring (130) is defined as a flat upper surface (132), flat outer surface (134), flat lower surface (136), and an inner surface (140) having a beveled upper edge (142) and a beveled lower edge (144), the retainer ring (130) has a split making it a non-continuous ring.

The spherical ball (20) contacts the locking ring (100), causing displacement from the locking ring slot (40) to the ring containment slot (118) housing the retainer ring (130). The beveled lower edge (112) on the locking ring (100) slidably engages the spherical ball (20) for ease of movement, while the upper surface (102) lifts the saddle member (60) by compression of the biasing springs (56, 58). The retainer ring (130) lower beveled edge (144) provides a ramp surface for use in expanding the diameter of the retainer ring (130), providing sufficient expansion for the spherical ball (20) to pass the ring containment slot (118) which temporarily houses the retainer ring (130) and locking ring (100). Once the widest diameter of the spherical ball (20) has passed the locking ring (100), the locking ring (100) is forced back into the locking ring slot (40). The retainer ring (130), in combination with the spring biased saddle member (60), snaps the locking ring back into the locking ring slot (40) with an audible sound and a movement that provides a tactile feel.

The set screw (50) can then be utilized to press the connecting rod (150) into contact with the saddle (60) placed over the spherical ball (20), simultaneously causing the lower portion of the spherical ball connector (20) to wedge against the inner surface (108) of the locking ring (100), immobilizing the connection. In the preferred embodiment, the saddle (60) employs compression springs (56, 58) to keep the connector assembly (30) in position during installation. This allows a surgeon to easily move the connector assembly (30) into a selected position, and the angular position of the connector assembly (30) will remain the same to facilitate installing of connecting rods (150). The system is modular; employing a collection of anchoring assemblies that are linked, via various connectors, to strategically arranged stabilizing rods. The connector assemblies are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Unique to this invention is the ability to lock the locking ring (100) into a position that prevents detachment of the spherical ball connector (20) from the connector assembly (30). This further allows a surgeon to attach various types of anchor members or the like to the connecting assembly, after having installed the bone anchor into the bone of a patient. While there are a myriad of anchoring devices that can be adapted to include the spherical ball, bone hooks, etc., for ease of illustration, the bone screw is depicted. It is well known that various lengths and diameters of bone screws are available, many of which would not fit through the inner diameter of the connector assembly. Thread styles, lengths and so forth that are best suited for installation may be estimated before surgery, but it is well known that only during actual surgery can the proper style be confirmed. Because it is most difficult to predict the proper combination of anchor screw and connector member, surgeons must either have a large selection of spinal implants to choose from, or be forced to use the closest combination and hope that it will suffice.

Figure 2:
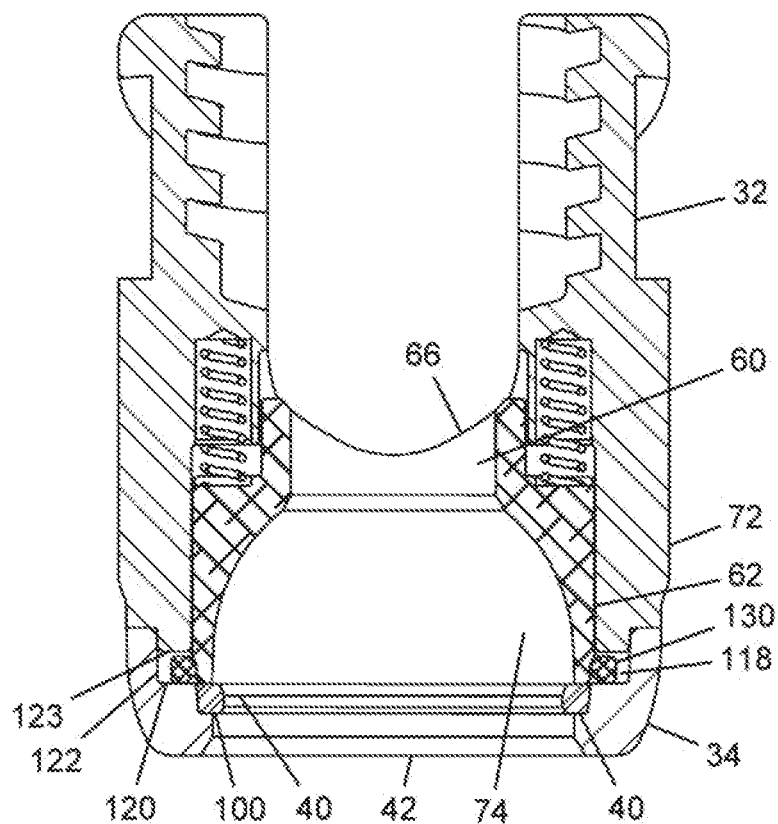
FIG. 2 is a cross-sectional side view of the connector assembly.

FIG. 2 is a cross-sectional side view of the connector assembly (32, 34) illustrating the lower cavity (74) with the locking ring (100) in the locking ring slot (40) and the retainer ring (130) in the ring containment slot (118).

Figure 3:
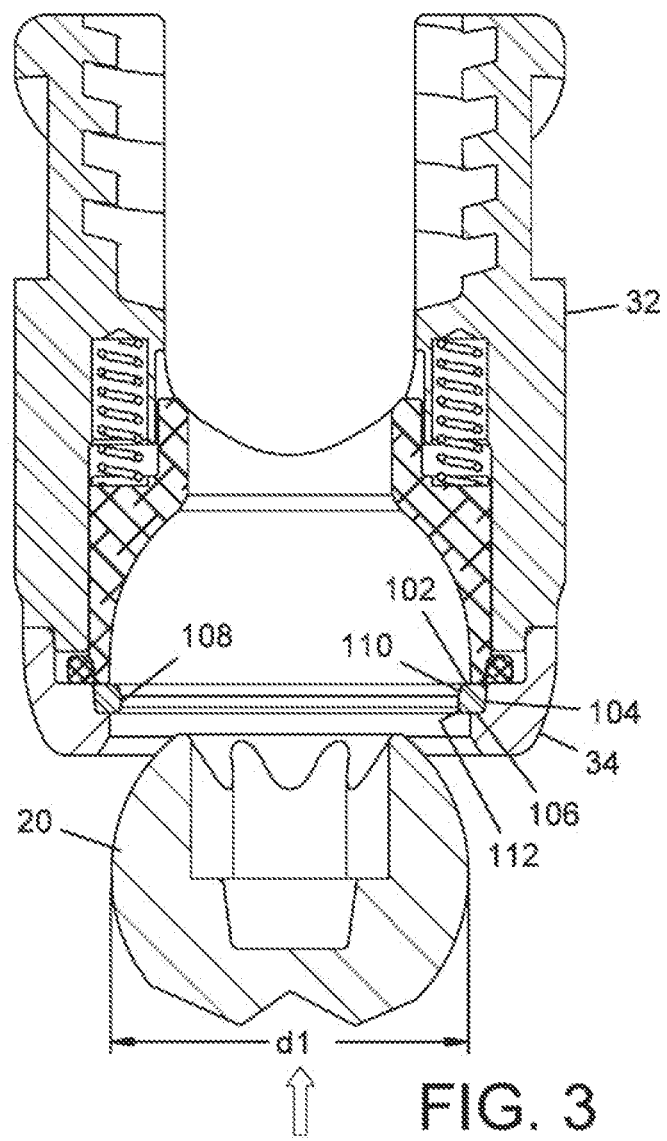
FIG. 3 is a cross-sectional side view of the connector assembly with a displaced spherical ball of a bone screw.

FIG. 3 is a cross-sectional side view with the spherical ball (20) upper surface (25) positioned to engage the locking ring (100) in the locking ring slot (40) of connector member (34).

Figure 4:
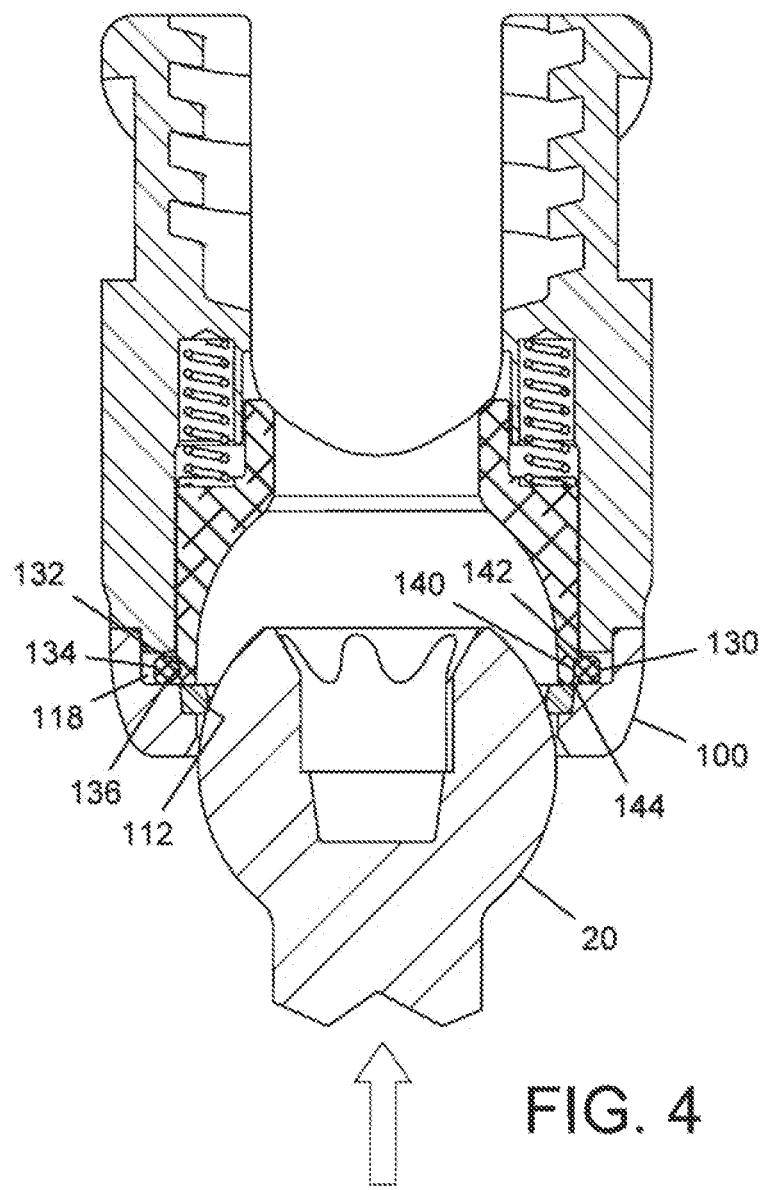
FIG. 4 is a cross-sectional side view of the connector assembly with the spherical ball engaging the locking ring in the locking ring slot.

FIG. 4 is a cross-sectional side view with the spherical ball (20) upper surface (25) contacting the lower beveled edge (112) of the locking ring (100).

Figure 5:
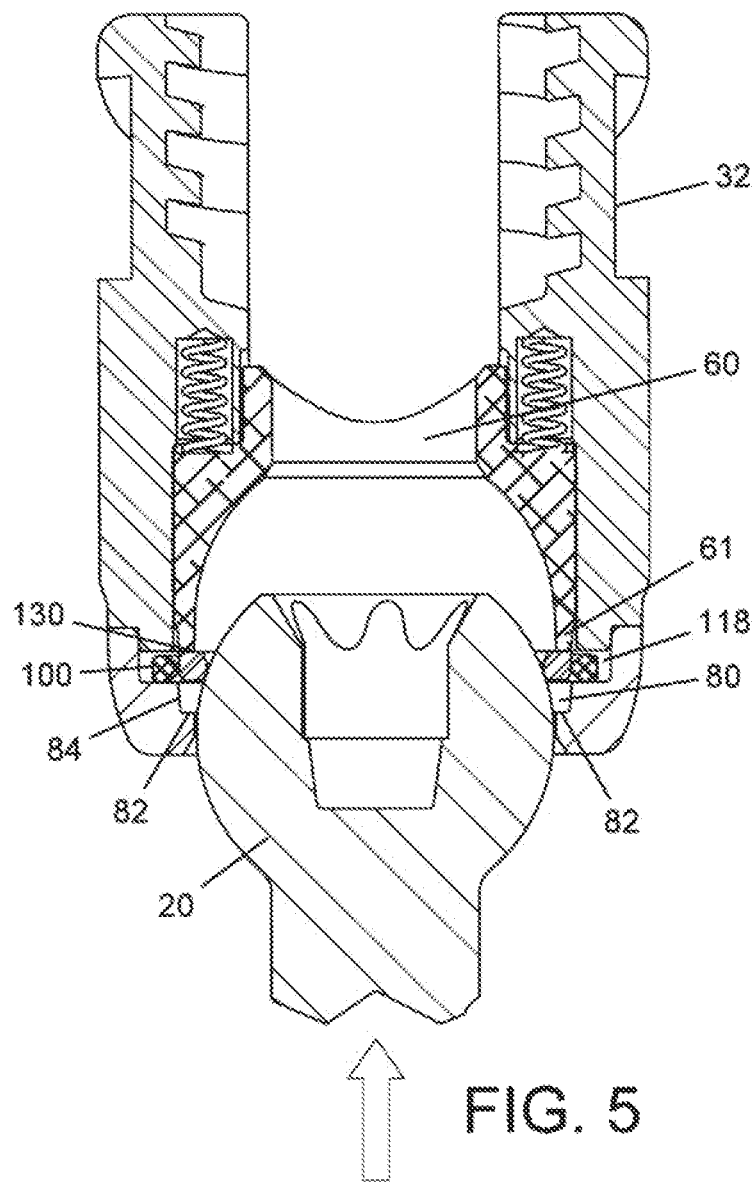
FIG. 5 is a cross-sectional side view of the connector assembly with the spherical ball placing the locking ring in the ring containment slot.

FIG. 5 is a cross-sectional side view of the spherical ball (20) placing the locking ring (100) in the ring containment slot (118); the lower end (61) of the saddle member (60) being forced upward by the locking ring (100), the upward movement constructed and arranged to be limited by the interface between the saddle member (60) and the lower connector member (34). It is noted that the ring containment slot (118) is sized to receive both the retainer ring (130) and the locking ring (100), with upward movement prohibited by the saddle (60).

Figure 6:
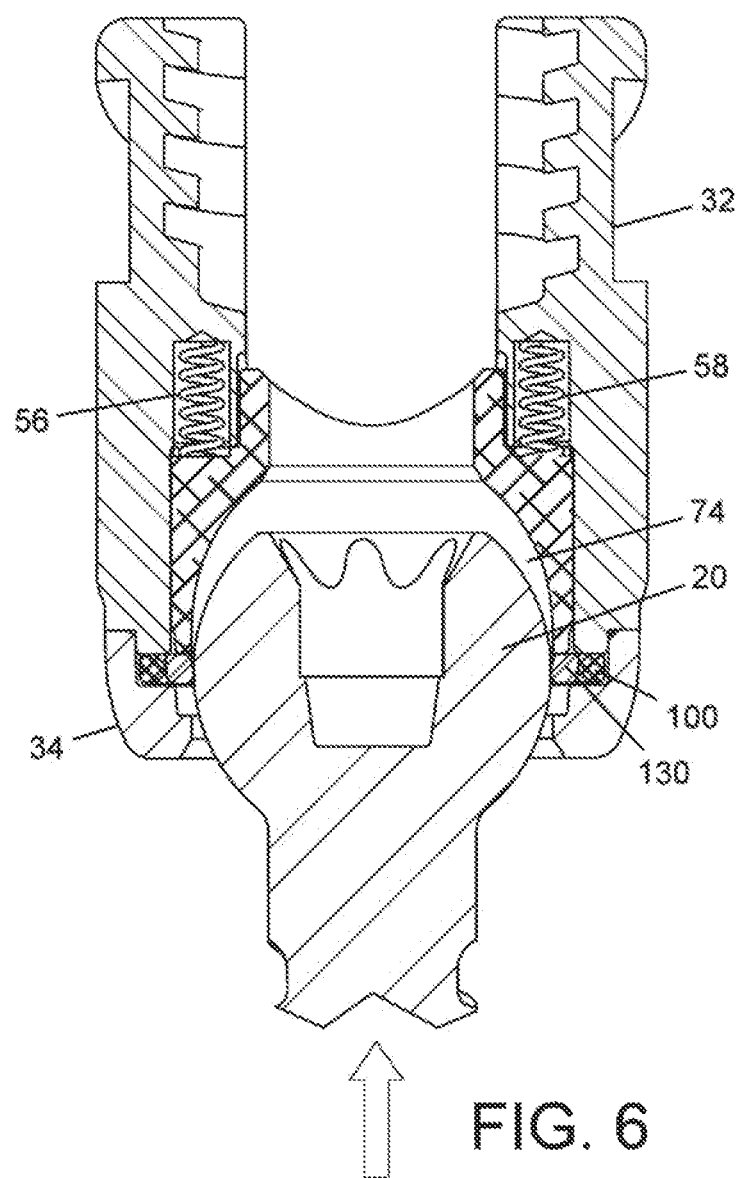
FIG. 6 is a cross-sectional side view of the connector assembly with the spherical ball causing the locking ring to expand the retainer ring.

FIG. 6 is a cross-sectional side view with the largest outer diameter of the spherical ball (20) forcing the locking ring (100) to expand the diameter of the retainer ring (130).

Figure 7:
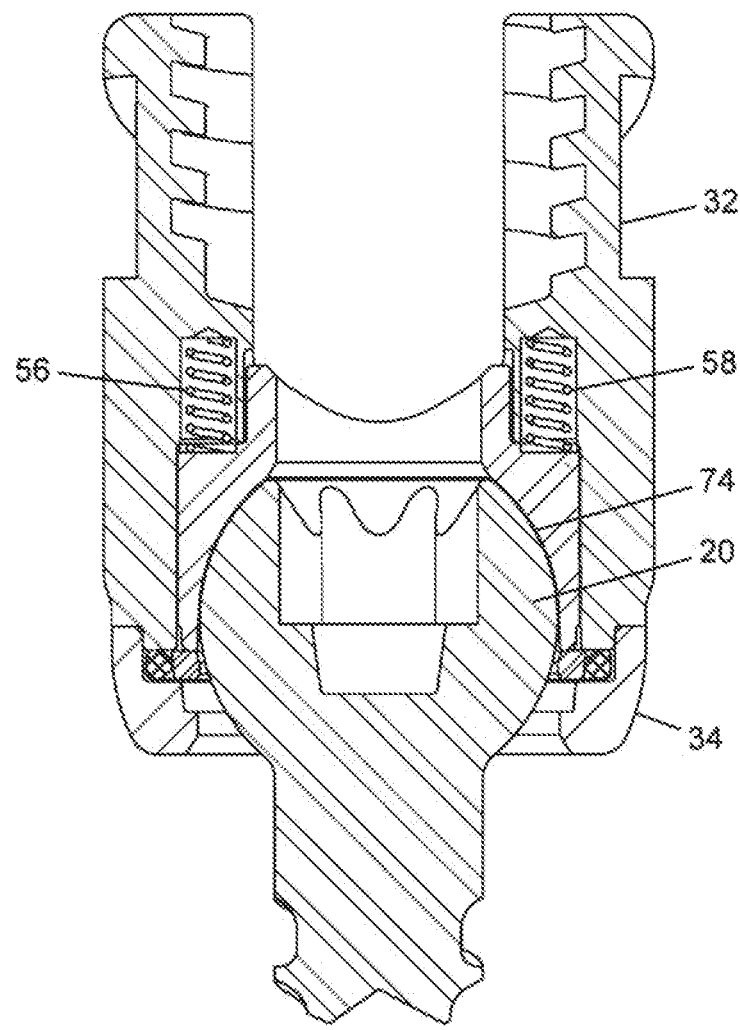
FIG. 7 is a cross-sectional side view of the connector assembly with the spherical ball passing the locking ring.

FIG. 7 is a cross-sectional side view of the spherical ball (20) within the cavity (74); the compression of the biasing springs (56, 58) limiting upward movement of the saddle member (60).

Figure 8:
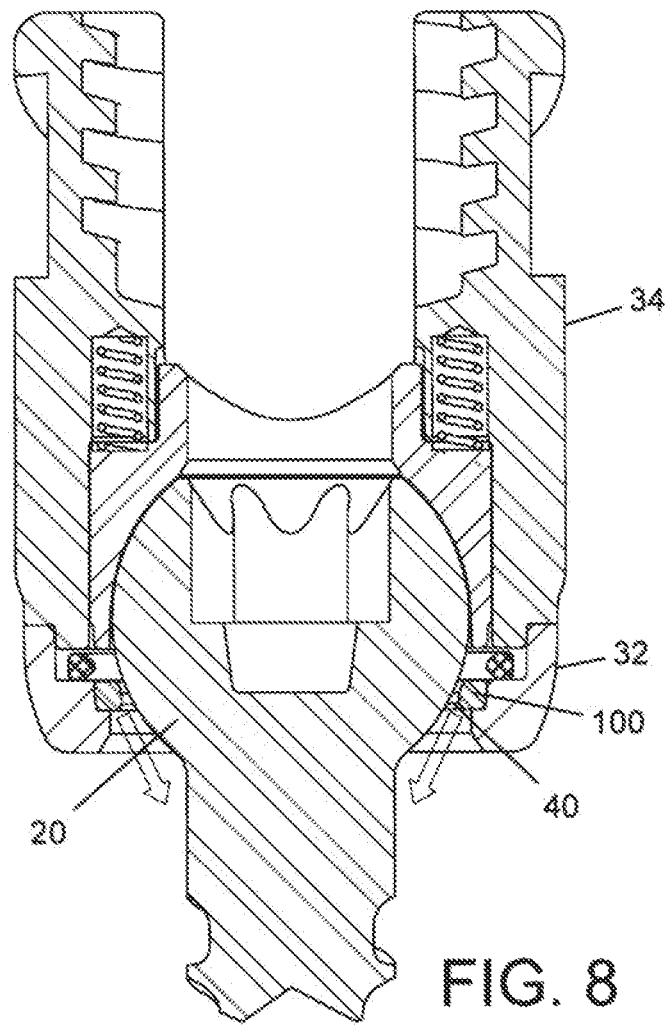
FIG. 8 is a cross-sectional side view of the connector assembly with the locking ring returned to the locking ring slot.

FIG. 8 is a cross-sectional side view illustrating the locking ring (100) returned to the locking ring slot (40).

Figure 9:
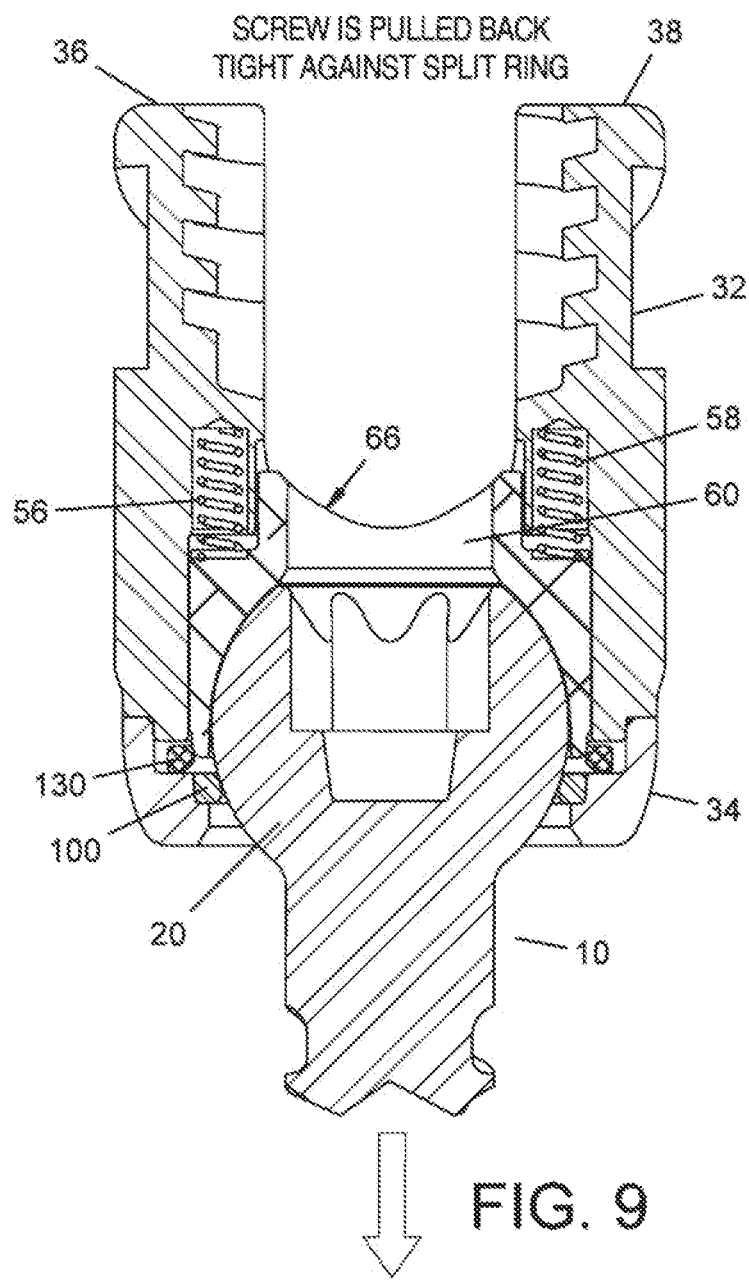
FIG. 9 is a cross-sectional side view of the connector assembly with the bone screw spherical ball permanently secured to the connector.

FIG. 9 is a cross-sectional side view of the connector assembly (32, 34) with the spherical ball (20) permanently secured to the connector assembly (32, 34) with the locking ring (100) wedged against the lower surface (27) of the spherical ball (20).

The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

All patents and publications mentioned in this specification are indicative of the levels of those skilled in the art to which the invention pertains. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures, and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A polyaxial ball and socket fastener comprising:
an anchor member formed from a shank having bone threads forming a proximal end, and a spherical ball having an upper surface and a lower surface forming a distal end; a connector assembly securable to said anchor member, said connector assembly having an upper section with a first side wall spaced apart from a second side wall forming a threaded opening therebetween, and a lower section having a continuous sidewall with a centrally disposed opening forming a lower cavity for receipt of said spherical ball, said lower section having a ring containment slot and a locking ring slot;
a retainer ring positioned within said ring containment slot, said retainer ring having a top wall, a bottom wall, a non-continuous outer side wall and an inner side wall having a beveled upper and lower edge;
a locking ring positioned within said locking ring slot, said locking ring having a top surface, a non-continuous outer side wall and an inner wall having a beveled upper and lower edge;
a saddle member slidably insertable into said opening, said saddle having an upper surface in alignment with said threaded opening for receipt of a rod member, and a lower spherical surface constructed and arranged to engage said upper surface of said spherical ball, wherein said spherical ball is coupled to said connector assembly by inserting through said centrally disposed opening by moving said locking ring from said locking ring slot into said ring containment slot, thereby expanding said retainer ring, allowing the upper surface of said spherical ball to enter said lower cavity, whereby said retainer ring forces said locking ring back into said locking ring slot and preventing removal of said spherical ball from said lower cavity; and
a set screw operatively associated with said threaded side walls, wherein the rod member is positioned on said upper surface of said saddle and secured thereto by said set screw, said set screw applying pressure to said upper surface of said spherical ball, whereby the lower surface of said spherical ball engages said locking ring to secure said anchor member in a fixed position.

2. The polyaxial ball and socket fastener according to claim 1, wherein said locking ring beveled lower edge is shaped to engage said upper surface of said spherical ball during said insertion, said locking ring having an outer surface shaped to engage said retainer ring beveled lower edge, wherein said locking ring is forced to move into said ring containment slot by expanding said retainer ring.

3. The polyaxial ball and socket fastener according to claim 1, wherein said saddle is spring biased.

4. The polyaxial ball and socket fastener according to claim 1, wherein a lower end of said saddle member engages an upper surface of said locking ring, and said inner surface of said retainer ring engages an outer surface of said saddle member before insertion of said spherical ball into said lower cavity.

5. The polyaxial ball and socket fastener according to claim 1, wherein said locking ring is constructed and arranged to indicate movement of said locking ring by tactile feel and sound when said locking ring is relocated from said ring containment slot to said locking ring slot.

6. The polyaxial ball and socket fastener according to claim 1, wherein said saddle member has a centrally disposed opening.

7. The polyaxial ball and socket fastener according to claim 6 wherein said spherical ball includes a driver receptacle accessible through said saddle member centrally disposed opening.

8. The polyaxial ball and socket fastener according to claim 1, wherein said locking ring beveled lower edge is shaped to engage said upper surface of said spherical ball during said insertion, said locking ring having an outer surface shaped to engage said retainer ring beveled lower edge, wherein insertion of said spherical ball forces said locking ring into said ring containment slot, causing the expanding of said retainer ring and said retainer ring forces said locking ring to return to said locking ring slot upon insertion of said spherical ball.

* * * * *